United States Patent [19]

Kern

[11] Patent Number: 4,719,235

[45] Date of Patent: Jan. 12, 1988

[54] METHODS AND COMPOSITIONS FOR TREATING VIRAL INFECTION

[75] Inventor: Gerald N. Kern, 4631 Louis Ave., Encino, Calif. 91316

[73] Assignee: Gerald N. Kern, Encino, Calif.

[21] Appl. No.: 732,363

[22] Filed: May 8, 1985

Related U.S. Application Data

[63] Continuation-in-part of Ser. No. 661,396, Oct. 16, 1984, abandoned.

[51] Int. Cl.$^4$ .......................... A61K 31/19; A61K 9/70
[52] U.S. Cl. ..................................... 514/547; 514/934; 424/443; 604/4
[58] Field of Search .................. 514/547, 934; 424/27; 604/4, 5

[56] References Cited

U.S. PATENT DOCUMENTS

| | | | |
|---|---|---|---|
| 2,028,091 | 1/1936 | Jaeger | 560/151 |
| 2,149,240 | 2/1939 | Crossley | 167/58 |
| 2,176,423 | 10/1939 | Jaeger | 560/151 |
| 2,574,526 | 11/1951 | Bordon et al. | 117/86 |
| 3,650,964 | 3/1972 | Sedliar et al. | 252/106 |
| 3,737,552 | 6/1973 | Gordon et al. | 514/552 |
| 3,873,721 | 3/1975 | Hargett | 514/552 |
| 3,942,512 | 3/1976 | Hargett | 128/1 |
| 3,984,570 | 10/1976 | Bent et al. | 514/718 |
| 4,013,418 | 3/1977 | Plakas | 23/253 |
| 4,066,786 | 1/1978 | Bent et al. | 514/552 |
| 4,096,311 | 6/1978 | Pietreniak | |
| 4,139,630 | 2/1979 | Asculai et al. | 514/461 |
| 4,148,872 | 4/1979 | Wagenknecht et al. | 424/48 |
| 4,156,715 | 3/1979 | Wagenknecht et al. | 424/48 |
| 4,156,716 | 3/1979 | Wagenknecht et al. | 424/48 |
| 4,157,385 | 6/1979 | Wagenknecht et al. | 424/48 |
| 4,161,517 | 9/1979 | Wagenknecht et al. | 424/48 |
| 4,256,763 | 3/1981 | McHugh | 514/470 |
| 4,307,143 | 12/1981 | Meitner | 252/91 |
| 4,334,910 | 6/1982 | Lorimez et al. | 71/82 |
| 4,514,385 | 4/1985 | Damani et al. | 424/81 |
| 4,540,566 | 9/1985 | Davis et al. | 424/22 |
| 4,578,265 | 3/1986 | Pellico et al. | 424/50 |

FOREIGN PATENT DOCUMENTS

| | | |
|---|---|---|
| 0107594 | 5/1984 | Fed. Rep. of Germany . |
| 53-113019 | 10/1978 | Japan . |
| 56-15202 | 2/1981 | Japan . |
| 2103089 | 7/1982 | United Kingdom . |

OTHER PUBLICATIONS

A. G. Gilman, L. S. Goodman and A. Gilman, The Pharmacological Basis of Therapeutics (1980), Sixth Edition, pp. 1008–1009.

Department of Health and Human Services, Food and Drug Administration, Report Docket No. 84N–0184. "Dioctyl Sodium Sulfosuccinate, Dioctyl Potassium Sulfosuccinate, and Dioctyl Calcium Sulfosuccinate; Availability of the Final Report of the DSS Scientific Review Panel, Mar. 1984.

Article titled "Bloat in Cattle. XVI. Development and Application of Techniques for Selecting Drugs to Prevent Feedlot Bloat", R. M. Meyer et al. (Kansas Agric. Exp. Stn., Kansas State Univ., Manhattan, Kans.), J. Admin. Sci., 1972, 34(2), 234–40.

Baker et al., "Action of Synthetic Detergents on the Metabolism of Bacteria", J. Exp. Med., 73 2490271 (1941).

Chemical Abstract (56:9226g), Belgian article titled "Bactericidal Properties of Anionic Detergents".

Article titled "Studies of the Anti-Microbial Activity of Nonionic and Anionic Surfactants", Chuichi Ishizeki (Eisei Shikensho, Japan), Eisei Shikenjo Hokoku, 1970 (88), 75–8.

Accepted Dental Therapeutics, 35th Ed., published by the American Association, Chicago, 1973, p. 265.

"Effects of Antiviral Agents on the Potato Y Virus in Intact Potato Plants. II. Antimetabolites and Other Antiviral Substances", Hans Hect et al. (Bayer. Landesanst. Bodenkult, Pflanzenbau, Freising. Ger.), Bayer, Landsirtsch Jahrb., 1978, 55(4), 433–57.

"Spraying Potatoes to Prevent Leaf Roll Spread by the Green Peach Aphid", W. A. Shands et al. (Univ. Maine, Orono, Maine), Amer. Potato J., 1972, 49(1), 23–34.

"Effects of Several Wetting Agents on the Viabiity of an Arthroaleuriosphorous Fungus", G. F. Orr et al. (Environ, Life Sci. Div., U.S. Army Dugway Proving Ground, Dugway, Utah), Bulletin, Torrey Botanical Club, 1977, 104(1), 25–8.

"The Effect of Post-Infectional Potato Tuber Metabolites and Surfactants on Zoospores of Oomycetes", Jane E. Harris et al. (A.R.C. Food Res. Inst., Norwich, Engl.), Physiol. Plan Pathol., 1977, 11(2), 163–9.

Eradication of the Perithecial Stage of Apple Scab with Surfactants", R. T. Burchill et al. (East Malling Res. Stn., Maidstone/Kent, Engl.), Ann. Appl. Biol., 1977, 87(2), 229–31.

(List continued on next page.)

Primary Examiner—J. R. Brown
Assistant Examiner—John W. Rollins, Jr.
Attorney, Agent, or Firm—Christie, Parker & Hale

[57] ABSTRACT

Methods and compositions are provided for treating selected viral infections wherein the anti-virally active ingredient is a compound of the following formula:

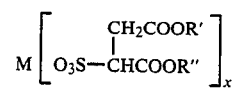

$$M\left[\begin{array}{c} CH_2COOR' \\ | \\ O_3S-CHCOOR'' \end{array}\right]_x$$

wherein R' and R'' are each independently a straight chain or branched chain alkyl group having from 5 to 8 carbon atoms, M is NH$_4$, Na, K or Ca, and x is 1 when M is NH$_4$, Na or K, and x is 2 when M is Ca.

37 Claims, No Drawings

OTHER PUBLICATIONS

"Effects of Some Surfactant Fungicides on Rhizobium Trifolii and Its Symbiotic Relationship with White Clover", D. J. Fisher et al. (Long Ashton Res. Stn., Univ. Bristol, Long Ashton/Bristol, Engl.), Ann. Appl. Biol., 1978, 90(1), 73–84.

"Effects of Fungicides and Surfactants on the Zoospores of Olpidium Brassicae", J. A. Tomlinson et al. (Natl. Veg. Res. Stn., Wellesbourne/Warwick, Engl., CV 359EF), Ann. Appl. Biol., 1979, 93(1), 13–19.

"Surfactants for the Control of Apple Mildew", Derek R. Clifford et al. (Long Ashton Res. Stn., Univ. Bristol, Bristol, Engl.), Pestic. Sci., 1975, 6(4), 409–18.

"Surfactants as Fungicides", F. R. Forsyth, Canadian Journal of Botany, 42 (1964), pp. 1335–1347.

"Greenhouse Evaluation of Chemicals for Control of Powdery Mildews", A. H. M. Kirby et al., Ann. of Appl. Biol. (1963), 52, pp. 45–54.

METHODS AND COMPOSITIONS FOR TREATING VIRAL INFECTION

CROSS-REFERENCE TO RELATED APPLICATION

This application is a continuation-in-part of application Ser. No. 661,396 filed Oct. 16, 1984 now abandoned, which is incorporated herein by this reference.

FIELD OF THE INVENTION

The field of this invention relates to anti-viral methods and anti-viral compositions. More particularly this invention relates to methods for treating viral infections in humans and animals, for preventing viral infections in humans and animals, for inactivating viruses on surfaces and articles and for anti-viral compositions for carrying out the aforementioned methods. Such compositions can include lotions, creams, ointments, salves, powders, sprays, capsules, tablets, suppositories and/or suspensions and solutions for administration by any route.

BACKGROUND OF THE INVENTION

Effective treatment of various viral infections has been a goal of medical researchers for years. One such virus that is a focus of recent research is Herpes Simplex virus. Herpes Simplex occurs in two antigenic types, Herpes febrilis and Herpes genitalis, referred to as Type 1 and Type 2 or HSV-1 and HSV-2, respectively. Infection is often manifested by the appearance of vesicular eruptions, herpetic lesions (commonly referred to as fever blisters or cold sores when they occur on or about the lips or mouth), or other clinical manifestations that can involve any part of the body. Persons with Herpes Simplex infections are likely to have recurrent periods of lesion development spaced by periods of remission.

While no cure is presently known for Herpes Simplex in either form, certain substances have been advanced for management of the disease. In U.S. Pat. No. 4,256,763 to McHugh a method for treating inflammatory viral infections such as Herpes Simplex and acne was disclosed involving the application of 3,3-bis(p-hydroxyphenyl)phthalide, in amounts up to 100 milligrams, preferably 15 to 30 milligrams initially and repetitively at predetermined intervals.

U.S. application Ser. No. 633,255 filed by me on July 23, 1984 discloses a method for treating Herpes Simplex infection condition which includes administering to a person having said condition an effective dosage of bisacodyl, i.e., phenol, 4,4'-(2-pyridinylmethylene)bis, diacetate ester.

There is a need in the art, however, for improved methods for treating Herpes Simplex infection in humans as well as a need for methods for treating various viral infections in both animal and human hosts caused by enveloped viruses other than Herpes Simplex. There is also a need in the art for improved methods for treating infections in both animal and human hosts caused by various non-enveloped viruses such as Rotavirus, which infects cattle and also can cause severe diarrhea and resulting death in human infants.

Preferably, the method provided for treating such viral infections incorporates the use of a single compound (ingredient) or family of compounds that can be administered to the animal or human topically or internally (systemically or locally) and which is effective against a plurality of viral infections caused by both enveloped and non-enveloped viruses.

Compositions are also needed for inactivating viruses on surfaces such as, for example, on bathroom and kitchen fixtures and the like.

SUMMARY OF THE INVENTION

The present invention is directed to a method for anti-viral treatment for humans and animals. One embodiment of the present invention is directed to a method for treating viral infections of humans and animals which comprises administering to the human or animal having such a viral infection an effective anti-viral dosage of a compound of the following formula:

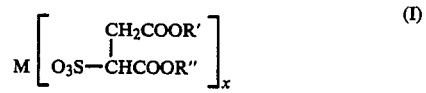

wherein R' and R" are each independently a straight chain or branched chain alkyl group having from 5 to 8 carbon atoms, M is a physiologically compatible group selected from NH$_4$, Na, K or Ca, and x is 1 when M is NH$_4$, Na or K and x is 2 when M is Ca.

Another embodiment of the present invention is directed to a method for treating a systemic or localized viral infection of animals and humans which comprises administering to the animal or human having a systemic viral infection an effective anti-viral dosage of a compound of the above Formula (I).

A further embodiment of the present invention is directed to a method for preventing a systemic or localized viral infection in an animal or human which comprises administering to the animal or human an effective anti-viral dosage of a composition of the above Formula (I).

An additional embodiment of the present invention is directed to a method for treating a superficial or cutaneous viral infection in an animal or human comprising topically applying (administering) to the external surface of the human or animal a composition containing an effective anti-viral amount of the composition of the above Formula (I). By external surface of a human or animal is meant the skin, eye surfaces, finger and toenails and mucous membranes.

Yet a further embodiment of the present invention is directed to a method for inactivating an enveloped virus on a surface comprising contacting such an enveloped virus with an anti-virally effective amount of a composition of the above Formula (I).

DETAILED DESCRIPTION

The anti-viral agent of the present invention is a compound of the following formula:

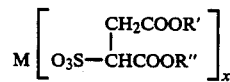

wherein R' and R" are each independently a straight chain or branched chain alkyl group of from 5 to 8 carbon atoms, M is a physiologically compatible group selected from NH$_4$, Na, Ca, K and the like, and x is 1 when M is NH$_4$, Na or K and x is 2 when M is Ca. The M group and the dosage of the compound of Formula (I) are selected such that concentration of M in the human or animal host receiving the anti-viral agent will be at a non-toxic level. Normally for systemic or local application and for most topical applications M will be Na, Ca, or K.

The R' and R" groups can be the same or different. Preferably, however, R' and R" will be the same. Typical R' and R" groups include amyl, octyl and 2-ethylhexyl; preferably R' and R" are both 2-ethylhexyl. In a preferred embodiment of the present invention, M is Na.

In a preferred embodiment of the present invention, the anti-viral agent of Formula (I) is dioctyl sodium sulfosuccinate [also known as 1,4-bis(2-ethylhexyl)-sodium sulfosuccinate, docusate sodium and DSS].

The effective dosage of the anti-viral agent is provided to the animal and human host in a delivery system which assures a systemic or local concentration of between about 0.01 and 0.2 mg of the anti-viral agent per ml of body fluids at the cellular level.

The term "systemic" as used herein with regard to concentration, means the concentration of the anti-viral agent per ml of body fluids at the cellular level within the body generally. The term "local" as used herein with regard to concentration, means the concentration of the anti-viral agent per ml of body fluids at the cellular level at a specific body site, for example, in a particular organ.

In accordance with practice of the method of this invention, viral infections in human or animal hosts are surprisingly susceptible to treatment by administering to the host an effective dosage of dioctyl sodium sulfosuccinate. Although the methods of this invention are described below with respect to docusate sodium, practice of principles of this invention is contemplated with anti-viral agents of the above Formula (I) which are equivalent to docusate sodium such as dioctyl calcium sulfosuccinate [1,4-bis(2-ethylhexyl)calcium sulfosuccinate] and dioctyl potassium sulfosuccinate [1,4-bis(2-ethylhexyl)potassium sulfosuccinate] and the like.

The term "treating a viral infection" as used herein means systemic or local administration of an amount of docusate sodium effective for inactivating a virus within the human or animal host, or topical administration of an amount of docusate sodium effective for inactivating a virus in a virus containing area of human or animal tissue.

As is described below in greater detail, viral infection of human or animal hosts can be prevented by contacting cells of the potential host with an effective amount of docusate sodium to prevent infections. Without being bound by theory, it is thought that such cell contact either inhibits adsorption of the virus by the cell, which thereby precludes entry of the virus into the cell, or deters the virus from replicating within the cell after entry has been made.

Docusate sodium, which is a wax-like solid that is slowly soluble in water and freely soluble in alcohol, can be suitably prepared by esterification of maleic anhydride with 2-ethylhexyl alcohol followed by addition of sodium bisulfite. The other compounds of Formula (I) can be prepared by esterification of maleic anhydride with the appropriate physiologically acceptable alcohol followed by the addition of the appropriate bisulfite salt, such as ammonium bisulfite, potassium bisulfite, and calcium bisulfite.

Docusate sodium is commonly used as a wetting agent in a variety of industrial, pharmaceutical and food additive applications. For example, it is used in cocoa, evaporated milk, cold packed cheese food, creme cheese and french dressing as an additive. As a pharmaceutical it is used as a stool softening agent.

To be effective as an anti-viral agent in accordance with practice of principles of the method of this invention when used systemically or locally, the concentration of docusate sodium in body fluids of the human or animal host at the cellular level must be at least about 0.01 milligrams (mg) of docusate sodium per milliliter (ml) of such fluids. This requires a dosage regimen of from about 5 mg to about 35 gms per day of docusate sodium in a delivery system which assures a systemic or local concentration of at least about 0.01 mg of docusate sodium per ml of body fluids at the cellular level.

Preferably, the concentration of docusate sodium in fluids at the cellular level is no greater than about 0.2 mg of docusate sodium per ml of such fluids to provide a safety factor thereby ensuring that there are no toxic side effects. In any event, while docusate sodium is used as a food additive and as a pharmaceutical stool softening agent, it is known that such uses do not provide an effective systemic or local concentration of from about 0.01 mg to about 0.2 mg of docusate sodium per ml of body fluids on a cellular level as is required for practice of this invention.

Docusate sodium can be administered orally, intravenously, subcutaneously, intramuscularly, intracutaneously, or by inhalation or by instillation into a body site or cavity. Regardless of the type of administration, it may be dispersed in a pharmaceutically acceptable carrier. For example, when administered orally, it can be in tablet or capsule carriers which can include components such as excipients, bulking agents, lubricants, disintegrants, and dyes and the like. It can also be administered orally in a suitable liquid carrier, for example, a carrier comprising ethanol or the like. The term "carrier" further includes vehicles useful in preparing the injection or intravenous forms of docusate sodium such as isotonic saline-type solutions and isotonic dextrose-type solutions, for example.

Docusate sodium can be administered topically in many forms. For example, it can be administered in lotion, cream, emulsion or spray form, for treating virally induced lesions such as herpetic lesions and the like. Additionally, it can be provided for administration in pharmaceutically acceptable mouthwash formulations for inactivating viruses in the oral cavity, e.g., HSV-1.

In further examples of vehicles for administration of docusate sodium, it may be provided in a pharmaceutically acceptable carrier for use as an aerosol spray for bronchial inhalation therapy, for instance. It may also be provided as the active anti-viral ingredient in a virucidally effective powder. Docusate sodium may also be provided in a cleanser formulation for use in disinfecting body surfaces or as a sanitizer for disinfecting surfaces such as bathroom and kitchen fixtures and the like.

In yet another example of techniques for using docusate sodium as a virucide, it may be provided in a pharmaceutically acceptable carrier for contacting any virus that may be in blood, plasma, serum or in products derived therefrom. Such contact can provide for inactivation of any virus, for example, Hepatitis B virus or HTLV III (AIDS) virus that may infect the blood, plasma, serum, or the products derived therefrom.

In a further exemplary embodiment of using docusate sodium as a virucide, a material such as a cellulosic web, can be used as a substrate or carrier for a virucidally effective amount of docusate sodium. Thus, for example, a facial tissue, bathroom tissue or hand towel or the like may be impregnated with a virucidally effective amount of docusate sodium. In one example, a person who has influenza disease caused by Influenza A virus uses a facial tissue impregnated with a virucidally effective amount of docusate sodium. Influenza A virus contacts the tissue and is inactivated. It is contemplated that the use of such a facial tissue can result in controlling spread of Influenza A virus.

Although the above embodiment is in the context of a facial tissue and Influenza A virus, other materials can be used, and viruses other than Influenza A can be inactivated. For example, non-woven substrates such as wet-creped hand towels and spunbonded and melt-blown polymeric webs commonly used in disposable hospital items such as surgical drapes, gowns, bedsheets, pillow cases and textile materials and the like can be impregnated with docusate sodium. For example, hygienic face masks used by persons suffering from respiratory illness can be impregnated with a virucidally effective amount of docusate sodium. Further, disposable diapers can be impregnated with docusate sodium as well as tampons and intravaginal sponges and the like. Docusate sodium may also be provided in an appropriate carrier as a vaginal douche.

The following are examples (non-limiting) of uses of docusate sodium as a virucide.

EXAMPLE 1

Topical Administration—Lotion

An exemplary embodiment of lotion prepared for topical administration for treating viral infection in accordance with practice of principles of this invention comprises 0.2% wt/wt docusate sodium, 5% wt/wt mineral oil, 4.5% wt/wt stearic acid, 3.5% wt/wt cetyl alcohol, 1.5% wt/wt triethanolamine, 0.15% wt/wt methylparaben, 0.05% wt/wt propylparaben with the remainder being deionized and filtered water.

The lotion is prepared in two phases, phase A which includes mineral oil, stearic acid, cetyl alcohol, and propylparaben and phase B which includes deionized and filtered water, triethanolamine, methylparaben and docusate sodium.

To prepare the lotion, an appropriate amount of mineral oil is metered into a jacketed stainless steel vessel. Into the same vessel, an appropriate amount of each of stearic acid, cetyl alcohol and propylparaben is measured. Moderate propeller agitation is provided and phase A (oil phase) is heated to 70° to 75° C. Mixing is continued until all solids are melted and a clear solution is obtained. Phase B is then obtained by weighing an appropriate amount of water into a jacketed stainless steel vessel (main mixing vessel) which is provided with both a propeller and a sweep agitation. Into the same vessel, an appropriate amount of each of triethanolamine, methylparaben and docusate sodium is added. With gentle propeller agitation phase B is brought to 72°–77° C. to obtain a clear solution. Phase A is then added to phase B which is at 72°–77° C. with continued propeller agitation. Mixing is continued for 20 minutes with the combined phases at about 70° to about 77° C. The batch is then cooled by introducing cooling water into the jacket of the vessel. Cooling is continued with moderate propeller agitation. When the batch begins to thicken agitation is continued until batch temperature reaches about 25° to about 30° C. A sample is then taken from both the top and bottom of the batch for quality control analysis.

The product is then ready to be placed into containers for topical application.

A person who has Herpes Simplex infection with active genital lesions applies the lotion to the lesion periodically. In one embodiment the lotion is applied every 4 hours. The treatment is continued until the lesions are healed.

While the above example illustrates the use of one exemplary lotion formulation, compositions are contemplated which included pharmaceutically acceptable carriers other than those of this embodiment. Additionally, the percentage of docusate sodium used can be different. For example, lotion formulations having as little as 0.001% to greater than 1% docusate sodium are contemplated.

EXAMPLE 2

Topical Administration—Mouthwash

An exemplary embodiment of a mouthwash prepared for topical administration for treating or preventing viral infection in accordance with practice of principles of this invention comprises 0.2% wt/wt docusate sodium, 5.0% wt/wt sorbitol solution, 10.0% wt/wt ethanol, and the remainder sterilized (deionized and filtered) water.

A person having an active lesion in the oral cavity from Herpes Simplex virus (HSV-1) takes from about 1 teaspoon full to about 4 teaspoons full of the mouthwash and places it into his mouth (oral cavity). The mouthwash is vigorously swished around in the mouth to thereby contact the Herpes Simplex virus associated with the lesion with a virucidally effective amount of docusate sodium. After 30 seconds or so the mouthwash is spit out. This procedure is repeated each several hours until the lesions are healed.

While the above example illustrates the use of one exemplary mouthwash formulation, formulations can be used which include pharmaceutically acceptable carriers other than those of this embodiment. Additionally, the percentage of docusate sodium used can be different. For example, mouthwash formulations having as little as 0.001% to greater than 1% docusate sodium are contemplated.

EXAMPLE 3

Topical Administration-Cleanser

An exemplary embodiment of a cleanser prepared for topical administration for treating or preventing viral infection in accordance with practice of principles of this invention comprises 23.3% sodium ($C_{14}$–$C_{16}$) olefin sulfonate, 5% myristamine oxide, 1% cocamidopropylbetaine, 3.5% lauramid DEA, 0.25% polyquaternium-7, 0.1% NaCl, 0.2% dioctyl sodium sulfosuccinate, a fragrance, a preservative with the remainder being water and containing sufficient citric acid to bring the pH of the cleanser to 7.

The cleanser is used to wash the external surface of the body for inactivating any enveloped virus on the surface which is contacted by the cleanser.

While the above example illustrates the use of one exemplary cleanser formulation, formulations can be used which include pharmaceutically acceptable carriers other than those of this embodiment. Additionally, the percentage of docusate sodium used can be different. For example, cleanser formulations having as little as 0.001% to greater than 1% docusate sodium are contemplated.

EXAMPLE 4

Surface Sterilization

An exemplary embodiment of a sanitizer prepared for disinfecting surfaces such as bathroom and kitchen fixtures and the like in accordance with practice of principles of this invention comprises about 0.2% wt/wt docusate sodium, about 10.0% wt/wt ethanol and the remainder water.

The solution is sprayed onto a bathroom fixture, for example onto a toilet seat so that any virus on the toilet seat is inactivated.

While the above example illustrates the use of one exemplary sanitizer composition, compositions comprising other ingredients can be used. Additionally, the percentage of docusate sodium can be different. For example, sanitizers having as little as 0.001% to greater than 10% docusate sodium are contemplated.

EXAMPLE 5

Systemic Administration Time/Sustained-Release Capsule

In one exemplary embodiment of practice of this invention for systemic treatment of viral infection, docusate sodium is provided in a time/sustained-release capsule form as is known in the art. From about 5 mg to about 35 gms of docusate sodium in such time release capsule form is administered per day to a person who has Herpes Simplex infection with active lesions. The dosage or form of drug administered is such that the systemic or local concentration of docusate sodium at the cellular level of the person being treated is from between 0.01 and 0.2 mg per ml. The treatment is continued until the lesions are healed.

EXAMPLE 6

Systemic Treatment-Tablet Form

In an exemplary embodiment of practice of this invention for systemic treatment, docusate sodium is administered in tablet form to a person prior to and during his exposure to HSV-2 for preventing infection. The dosage is such that the systemic or local concentration of docusate sodium at the cellular level is maintained at from about 0.01 to 0.2 mg per ml.

EXAMPLE 7

Inactivating Virus in Virus Contaminated Plasma

In an exemplary embodiment of practice of principles of this invention for inactivating a virus in a blood product, 500 ml of plasma infected with Hepatitis B virus is provided. A solution comprising 1 mg/ml of docusate sodium is formulated in a 0.85% sterile saline solution in accordance with this invention. One ml of the docusate sodium saline solution per 9 ml of the infected plasma is gently mixed with the plasma. The docusate sodium contacts the Hepatitis B virus in the plasma to thereby inactivate the Hepatitis B virus.

EXAMPLE 8

Inactivating a Virus Using a Facial Tissue Impregnated with Docusate Sodium A cellulosic web facial tissue is impregnated with a virucidally effective amount of docusate sodium. For example, docusate sodium is present in an amount of from about 0.01% to about 3% or more based on the total weight of docusate sodium and the weight of the tissue.

A person who has the flu, caused by the Influenza A virus, then uses the tissue for inactivating any Influenza A virus that contacts the tissue.

The following examples related to in vitro tests of the effect of dioctyl sodium sulfosuccinate on various viruses.

EXAMPLE 9

Titration of HSV-2 After Contact with Serum-Free Solutions Containing Docusate Sodium HSV-2 was suspended in eight different saline solutions as shown in Table 1 below. Seven of the solutions included docusate sodium at various concentrations, namely, 0.01, 0.02, 0.03, 0.04, 0.05, 0.1 and 0.2 mg of docusate sodium per ml of 0.85% saline solution. The eighth solution (the control) was a 0.85% saline solution free of docusate sodium. Each of the aforementioned solutions was incubated at 37° C. for fifteen minutes. At the end of the incubation period 0.1 ml samples were taken of each of the eight solutions and diluted in phosphate buffered saline. 0.2 ml aliquots of the diluted samples were then inoculated onto monolayers of MA-104 cells. After 1 hour at 37° C. the inoculated monolayers were overlayed with agar and the cultures were then incubated at 37° C. for 3 days to allow for plaque development. The agar overlay was then poured off, the monolayers stained with ethanolic crystal violet and the plaques counted. Virus inactivation was calculated for each sample from the ratio of the number of plaques in each such sample treated with docusate sodium to the total number of plaques in the control sample which was free of docusate sodium.

TABLE 1

| | Solution No. | | | | | | | |
|---|---|---|---|---|---|---|---|---|
| | (1) (control) | (2) | (3) | (4) | (5) | (6) | (7) | (8) |
| mg/ml docusate sodium | 0 | 0.2 | 0.1 | 0.05 | 0.04 | 0.03 | 0.02 | 0.01 |
| % Inactivation of HSV-2 | — | 100 | 100 | 100 | 100 | 97 | 70 | 19 |

From Table 1 it can be seen that docusate sodium in concentrations as low as 0.02 mg of docusate sodium per ml of solution effectively inactivates HSV-2.

EXAMPLE 10

Titration of HSV-2 After Contact with Docusate Sodium Solutions Containing Fetal Calf Serum The same procedure that was used for Example 9 was used for this example except that there were five different solutions used and each of the solutions contained 10% fetal calf serum. The concentration of docusate sodium in each of the solutions is shown in Table 2 along with the results of the experiment.

TABLE 2

| | Solution No. | | | | |
|---|---|---|---|---|---|
| | (1) (control) | (2) | (3) | (4) | (5) |
| mg/ml | 0 | 0.2 | 0.1 | 0.05 | 0.01 |

TABLE 2-continued

| | Solution No. | | | | |
|---|---|---|---|---|---|
| | (1) (control) | (2) | (3) | (4) | (5) |
| docusate sodium % Inactivation of HSV-2 | — | 95 | 10 | (not avail.) | 10 |

From Table 2 it can be seen that higher concentrations of docusate sodium were required for a given percentage of HSV-2 inactivation when the docusate sodium solution contained 10% fetal calf serum than when fetal calf serum was absent, e.g., as is the case with Example 9.

EXAMPLE 11

Titration of Rotavirus Strain SA-11 After Contact with Solutions Containing Docusate Sodium Rotavirus strain SA-11 was suspended in two different saline solutions as shown in Table 3 below; one solution included normal 0.85% saline with docusate sodium added to a final concentration of 0.2 mg/ml. The second solution (the control) was a 0.85% saline solution free of docusate sodium. After 15 minutes and 1 hour, 0.1 ml samples of each of the solutions were taken and appropriately diluted in phosphate buffered saline. 0.2 ml aliquots of the diluted samples were then inoculated onto monolayers of MA-104 cells. The monolayers were overlayed with agar and incubated at 37° C. for 3 days. The agar overlay was poured off, the cell monolayers stained with crystal violet and the plaques counted. Virus inactivation was calculated for each sample from the ratio of the number of plaques in the sample treated with docusate sodium to the total number of plaques in the control sample which was free of docusate sodium.

TABLE 3

| | plaque forming units (pfu/ml) | |
|---|---|---|
| Exposure Time In Minutes | Control | 0.2 mg/ml docusate sodium |
| 0 | 17,000 | 16,000 |
| 15 | — | 19,000 |
| 60 | 13,000 | 27,000 |

The above test was repeated using docusate sodium at a concentration of 1 mg/ml. The results of this test are shown in Table 4.

TABLE 4

| | pfu/ml | |
|---|---|---|
| Exposure Time In Minutes | Control | 1 mg/ml docusate sodium |
| 0 | 46,500 | 45,000 |
| 60 | 49,000 | 51,000 |

From Tables 3 and 4 it can be seen that under the experimental conditions used in Example 11, docusate sodium did not inactivate Rotavirus SA-11.

EXAMPLE 12

Titration of Coxsackievirus B-5 After Contact with Solutions Containing Docusate Sodium The same procedure used in Example 11 was used in this example with the exception that Coxsackievirus B-5 was substituted for Rotavirus SA-11. The results of this experiment are shown in Table 5.

TABLE 5

| | pfu/ml | |
|---|---|---|
| Exposure Time In Minutes | Control | 0.2 mg/ml docusate sodium |
| 0 | 30,000 | 12,500 |
| 15 | — | 23,000 |
| 60 | 25,500 | 30,000 |

From Table 5 it can be seen that under the experimental conditions used in Example 12, docusate sodium did not inactivate Coxsackievirus B-5.

EXAMPLE 13

Inactivation of Respiratory Syncytial Virus by Docusate Sodium

Respiratory syncytial virus (RSV) was suspended in two different saline solutions as shown in Table 6 below. One solution which contained normal 0.85% saline with docusate sodium was added to a final concentration of 0.1 mg/ml. The second solution (the control) was a 0.85% saline solution free of docusate sodium. After 15 minutes, 0.1 ml samples were taken and appropriately diluted in phosphate buffered saline. 0.2 ml aliquots of the diluted samples were then inoculated onto monolayers of HeLa cells. Virus infectivity was determined by cytopathic effects (CPE), which, in the case of RSV, is the formation of large multinucleate structures called syncytia. The results shown in Table 6 below are reported as the virus dilutions which contained sufficient infective particles to cause the formation of CPE in the cell monolayers.

TABLE 6

| | Presence of CPE | |
|---|---|---|
| Virus Dilution | Control | 0.1 mg/ml docusate sodium |
| $10^{-1}$ | + | — |
| $10^{-2}$ | + | — |
| $10^{-3}$ | + | — |
| $10^{-4}$ | — | — |
| $10^{-5}$ | — | — |

+ = CPE present
− = CPE absent

As shown in Table 6, RSV was inactivated by 0.1 mg/ml docusate sodium solutions.

EXAMPLE 14

Inactivation of Influenza A Virus by Docusate Sodium

Influenza A virus was suspended in two different saline solutions as shown in Table 7 below. One solution included normal 0.85% saline with docusate sodium added to a final concentration of 0.1 mg/ml. The second solution (the control) was a 0.85% saline solution free of docusate sodium. After 15 minutes, 0.1 ml samples were taken and appropriately diluted in phosphate buffered saline. 0.2 ml aliquots of the diluted samples were then inoculated onto monolayers of MDCK cells. Virus infectivity was determined on MDCK cells by the presence of CPE and by hemadsorption. Cells infected with influenza virus acquire the ability to absorb red blood cells as a result of viral proteins present in the cell membranes. Thus, determination of infectivity is less quantitive than for plaque forming viruses. Results are reported as the virus dilution which contained sufficient virus to cause CPE in the MDCK cells.

TABLE 7

| Virus Dilution | Presence of CPE | |
|---|---|---|
| | Control | 0.1 mg/ml docusate sodium |
| $10^{-1}$ | + | − |
| $10^{-2}$ | + | − |
| $10^{-3}$ | − | − |
| $10^{-4}$ | − | − |

As is shown in Table 7, Influenza A virus was readily inactivated by 0.1 mg/ml docusate sodium solutions.

EXAMPLE 15

Titration of Adenovirus After Contact with Solutions Containing Docusate Sodium

The same procedure used in Example 11 was used in this example except that Adenovirus was substituted for Rotavirus strain SA-11 and HeLa cells were substituted for MA-104 cells. The results of this experiment are shown in Table 8.

TABLE 8

| Exposure Time In Minutes | pfu/ml | | % Inactivation |
|---|---|---|---|
| | Control | 0.2 mg/ml docusate sodium | |
| 60 | 180,000 | 150,000 | 17 |

From Table 8 it can be seen that under the experimental conditions used in this example, docusate sodium solution at 0.2 mg/ml did not have a significant effect on Adenovirus replication at a contact time of 60 minutes.

EXAMPLE 16

Effectiveness of Mouthwash Formulation on HSV-2

A mouthwash formulation as disclosed in Example 2 was tested at various water dilutions to determine its effect on HSV-2 virus.

HSV-2 virus was suspended in six different mouthwash solutions as shown in Table 9 below. Four of the solutions included docusate sodium at various concentrations, namely 0.1, 0.05, 0.025, and 0.01 mg of docusate sodium per ml of mouthwash solution. The fifth solution (the control) was a 0.85% saline solution free of docusate sodium. The sixth solution (the placebo) was identical to the mouthwash solution except that it was free of docusate sodium.

Each of the aforementioned solutions was incubated at 37° C. for fifteen minutes.

At the end of the incubation period 0.1 ml samples were taken of each of the six solutions and diluted in phosphate buffered saline. 0.2 ml aliquots of the diluted samples were then inoculated onto monolayers of MA-104 cells. After 1 hour at 37° C. the inoculated monolayers were overlayed with agar and the cultures were then incubated at 37° C. for 3 days to allow for plaque development. The agar overlay was then poured off, the monolayers stained with ethanolic crystal violet and the plaques counted. The results are shown in Table 9 below.

TABLE 9

| | Mouthwash Solution No. | | | | | |
|---|---|---|---|---|---|---|
| | (1) (Control) | (2) (Placebo) | (3) | (4) | (5) | (6) |
| mg/ml-docusate | 0.0 | 0.0 | 0.1 | 0.05 | 0.025 | 0.01 mg/ml |
| sodium plaque forming units /ml (pfu/ml) | 57,000 | 50,000 | 0 | 0 | 0 | 0 |

EXAMPLE 17

Cytotoxicity of Docusate Sodium in Solutions Free of Serum

The cell lines used to evaluate cytotoxicity of docusate sodium were MA-104 derived from monkey kidneys, HeLa derived from human uterine carcinoma and primary fibroblasts from human foreskin. The cells were grown to confluency in 60×15 mm dishes. The cell monolayers were washed free of growth medium and 5 ml of serum-less growth medium containing docusate sodium at various concentrations was added. The curtures were incubated 24 hours at 37° C. and the cells then examined microscopically for cytotoxic effects (CTE). Controls were done in the same manner except that they were not exposed to docusate sodium.

Table 10 lists the cytotoxicity of docusate sodium with regard to selected cell lines in cell culture.

TABLE 10

| | mg/ml Docusate Sodium Solution | | | | |
|---|---|---|---|---|---|
| | (1) | (2) | (3) | (4) | (5) |
| CELLTYPE | 0 | 0.2 | 0.1 | 0.05 | 0.01 |
| MA-104 (toxicity) | 0* | 4+** | 4+ | 4+ | 0 |
| HeLa (toxicity) | 0 | 4+ | 4+ | 4+ | 0 |
| Foreskin (toxicity) | 0 | 4+ | 4+ | 4+ | 0 |

\* = Cells had normal morphology
\*\* = >90% of cells showed CTE.

As is shown in Table 10, docusate sodium was toxic to the cells when the concentration of docusate sodium in the solution described in this example was between 0.01 and 0.05 mg/ml.

EXAMPLE 18

Cytotoxicity of Docusate Sodium in Solutions Containing Serum

The same procedure that was used for Example 17 was used for this Example except that the medium used for growing the cells contained 2% by volume fetal calf serum.

Table 11 lists the cytotoxic effect of docusate sodium at various concentrations in selected cell lines in the cell cultures of this Example.

TABLE 11

| | mg/ml Docusate Sodium Solution No. | | | | |
|---|---|---|---|---|---|
| | (1) (control) | (2) | (3) | (4) | (5) |
| CELLTYPE | 0 | 0.04 | 0.03 | 0.02 | 0.01 |
| MA-104 (Cytotoxic effect) | 0* | 0 | 0 | 0 | 0 |
| HeLa (Cytotoxic effect) | 0 | 4+** | ±c*** | 0 | not avail. |
| Foreskin (Cyto- | 0 | 4+ | 4+ | ±c | 0 |

TABLE 11-continued

| | mg/ml Docusate Sodium | | | | |
|---|---|---|---|---|---|
| | Solution No. | | | | |
| | (1) (control) | (2) | (3) | (4) | (5) |
| toxic effect) | | | | | |

\* = Cells have normal morphology
\*\* = >90% of cells showed CTE.
\*\*\* = less than 10% of cells showed CTE.

The results presented in Table 11 indicated that the presence of serum reduced the cytotoxicity of docusate sodium. The results also indicated that MA-104 cells were less sensitive to docusate sodium than were HeLa and foreskin fibroblast cells.

EXAMPLE 19

Pretreatment of MA-104 Cells with Docusate Sodium Solution Prior to Exposure to HSV-2

In this Example the effect that initially contacting (pretreating) MA-104 cells with docusate sodium has on subsequent exposure of such pretreated cells to HSV-2 virus was studied.

MA-104 cells were washed free of growth medium and the cells were exposed to 0.02 mg/ml docusate sodium in serum-less growth medium for one hour. The docusate sodium solution was poured off, the cells washed twice, and then exposed to appropriately diluted HSV-2. A control solution prepared as above except for exposure to docusate sodium was also provided. After one hour at 37° C., the cells were overlayed with agar and incubated for 3 days at 37° C. to allow plaques to develop.

The results of this experiment are shown in Table 12 below.

TABLE 12

| | Solution | |
|---|---|---|
| | (1) | (2) |
| mg/ml docusate sodium | 0 | 0.02 |
| plaque forming units/ml (pfu/ml) | 548 | 26 |
| % decrease in pfu | — | 95 |

Table 12 shows that pretreating MA-104 cells with a docusate sodium solution containing 0.02 mg docusate sodium per ml of solution resulted in a substantial drop in plaque formation. This result is thought to be due to the docusate sodium reacting with the cells thereby causing inhibition of HSV-2 adsorption by the cell (thus inhibiting entry of HSV-2 into the cell) and/or by interference with virus replication once cell entry has been made.

EXAMPLE 20

Treatment of Cells Infected with HSV-2

MA-104 cells were washed free of growth medium and exposed to appropriately diluted HSV-2 for one hour at 37° C. At 6 and 24 hours after infection, the MA-104 cells were exposed to a solution containing 0.02 mg of docusate sodium per ml of solution for one hour at 37° C. The docusate sodium solution was poured off, agar overlay added, and the exposed cells incubated for 3 days at 37° C. to provide for plaque development.

This experiment indicated that under the conditions of this Example, docusate sodium contact was not effective in inactivating HSV-2 virus in cells infected with HSV-2 prior to docusate sodium contact.

EXAMPLE 21

Pretreatment of MA-104 Cells with Docusate Sodium Solution Prior to Exposure to Rotavirus The same procedure that was used for Example 19 was used for this Example except that the MA-104 cells were exposed to Rotavirus instead of HSV-2, the docusate sodium solution contained 0.05 mg of docusate sodium per ml of solution, and the MA-104 cells were exposed to the docusate sodium solution for 15 minutes instead The results of this experiment are shown in Table 13 below.

TABLE 13

| | Solution | |
|---|---|---|
| | (1) (control) | (2) |
| mg/ml docusate sodium | 0 | 0.05 |
| % decrease in pfu | — | 70 |

Table 13 shows that pretreating MA-104 cells with a docusate sodium solution containing 0.05 mg docusate sodium per ml of solution resulted in a 70% drop in plaque formation. As was the case for Example 19, this result is thought to be due to docusate sodium reacting with the MA-104 cells causing inhibition of Rotavirus adsorption by the cell and/or interference with virus replication once cell entry has been made.

EXAMPLE 22

Pretreatment of MA-104 Cells with Docusate Sodium Solution Prior to Exposure to Rotavirus The same procedure was used for this example as was used for Example 21 except that solutions containing 0.04 mg/ml, 0.07 mg/ml and 0.10 mg/ml of docusate sodium were used.

The results of this experiment are shown in Table 14 below.

TABLE 14

| | Solution | | | |
|---|---|---|---|---|
| | (1) (control) | (2) | (3) | (4) |
| mg/ml docusate sodium | 0 | 0.04 | 0.07 | 0.10 |
| % decrease in pfu | — | 10% | cytotoxic | cytotoxic |

EXAMPLE 23

Pretreatment of MA-104 Cells with Docusate Sodium Solution Prior to Exposure to Coxsackievirus B-5

The same procedure was used for this example as was used for Example 21 except that a solution containing 0.02 mg/ml of docusate sodium was used, and Coxsackievirus B-5 was substituted for Rotavirus.

The results of this experiment are shown in Table 15 below.

TABLE 15

|  | Solution | |
|---|---|---|
|  | (1) (control) | (2) |
| mg/ml docusate sodium | 0 | .02 |
| pfu/ml | 1,000,000 | 1,800,000 |

From Table 15 it can be seen that under the experimental conditions used in this example, there was no effect on plaque formation (infectivity) by docusate sodium.

EXAMPLE 24

Pretreatment of HeLa Cells with Docusate Sodium Solution Prior to Exposure to Respiratory Syncytial Virus The same procedure was used for this example as was used for Example 21 except that HeLa cells were substituted for MA-104 cells, the docusate sodium solution contained 0.1 mg/ml of docusate sodium, and Respiratory Syncytial Virus was substantial for Rotavirus. Three experiments were run.

Virus infectivity was determined by cytopathic effects (CPE). The results in Table 16 below are reported as the virus dilutions which contained sufficient infective particles to cause the formation of CPE in cell monolayers.

TABLE 16

| Experiment Number | Virus Dilution | Presence of CPE | |
|---|---|---|---|
|  |  | Control | 0.1 mg/ml docusate sodium |
| 1 | $10^{-1}$ | + | +$^a$ |
|  | $10^{-2}$ | + | − |
|  | $10^{-3}$ | − | − |
|  | $10^{-4}$ | − | − |
| 2 | $10^{-1}$ | + | + |
|  | $10^{-2}$ | + | + |
|  | $10^{-3}$ | + | +$^a$ |
|  | $10^{-4}$ | − | − |
| 3 | $10^{-1}$ | + | − |
|  | $10^{-2}$ | + | − |
|  | $10^{-3}$ | − | − |
|  | $10^{-4}$ | − | − |

$^a$ = Fewer syncytia on pretreated cells than on corresponding controls.

It is clear from the results in Table 16, that pretreatment with docusate sodium confers partial protection on HeLa cells against RSV infection.

EXAMPLE 25

Pretreatment of HeLa Cells with Docusate Sodium Prior to Exposure to Adenovirus

HeLa cells were washed free of growth medium and the cells were exposed to 0.125 mg/ml docusate sodium in 10% fetal calf serum MEM for 15 minutes. The docusate sodium solution was poured off, the cells rinsed with phosphate buffered saline and then exposed to appropriately diluted Adenovirus. A control solution prepared as above except for exposure to docusate sodium was also provided. After one hour at 37° C., the cells were overlayed with agar and incubated for 3 days at 37° C. to allow plaques to develop.

The results of this experiment are shown in Table 17 below.

TABLE 17

|  | Solution | |
|---|---|---|
|  | (1) | (2) |
| mg/ml docusate sodium | 0 | 0.125 |
| plaque forming units/ml | 180,000 | 175,000 |
| % decrease in pfu | — | 3 |

EXAMPLE 26

Pretreatment of MDCK Cells with Docusate Sodium Prior to Exposure to Influenza A Virus The same procedure was used for this example as was used for Example 24 except that MDCK cells were substituted for HeLa cells and Influenza A virus was substituted for Respiratory Syncytial Virus. Two experiments were run.

The results of these experiments are shown in Table 18 below.

TABLE 18

| Experiment Number | Virus Dilution | Presence of CPE | |
|---|---|---|---|
|  |  | Control | 0.1 mg/ml docusate sodium |
| 1 | $10^{-1}$ | + | − |
|  | $10^{-2}$ | + | − |
|  | $10^{-3}$ | − | − |
|  | $10^{-4}$ | − | − |
| 2 | $10^{-1}$ | + | +− |
|  | $10^{-2}$ | + | − |
|  | $10^{-3}$ | − | − |
|  | $10^{-4}$ | − | − |

EXAMPLE 27

Duration of Effect of Pretreatment of MA-104 Cells Prior to Exposure to HSV-II

MA-104 cell monolayers were washed twice with Earle's basal salt solution (EBSS) and a 0.02 mg/ml solution of docusate sodium was added to each culture dish. The culture dishes were incubated at 37° C. for one hour and the docusate sodium solutions poured off. The monolayers were then washed twice with EBSS and at appropriate time intervals infected with HSV-II. After the addition of overlay agar, the cultures were incubated at 37° C. for 3 days, stained with crystal violet, and the plaques counted. Control cultures were treated in a similar manner except for exposure to docusate sodium. Results of these experiments are described in Table 19 below.

TABLE 19

| Hours After Exposure to Docusate Sodium at time of infection | pfu/ml | | % Reduction In Infectivity |
|---|---|---|---|
|  | Control | 0.02 mg/ml docusate sodium |  |
| 0 | 270,000 | 53,000 | 81 |
| 2 | 30,000 | 14,000 | 54 |
| 24 | 69,000 | 69,000 | 0 |
| 72 | 69,000 | 58,000 | 16 |

The results in Table 19 indicate the anti-herpes effect produced by pretreating cells under experimental conditions used in this example is transitory.

EXAMPLE 28

Recovery of Herpes Virus from a Contaminated Surface

Glass microscope slides were cleaned with ethyl alcohol and sterlized in an autoclave. The slides were placed in sterile petri dishes and 0.1 ml of herpes virus suspended in 5% blood serum was spread in the slides. Sterile air was passed over the slides until the smear was dried (about 10 minutes). 0.9 ml of phosphate buffered saline was added to a first smear (the control smear) and 0.4% dioctyl sodium sulfosuccinate in phosphate buffered saline was added to a second smear and the virus smears were then removed with a sterile rubber policeman. The recovered virus suspension samples were appropriately diluted in phosphate buffered saline and plaque forming units determined on MA-104 cells using the same procedure as was used in Example 11. The results are shown in Table 20 below.

TABLE 20

|  | Control | Control Smear | Docusate Sodium Smear |
|---|---|---|---|
| Plaque forming units | 41,250 | 13,500 | 0 |

From Table 20 it can be seen that about 30% of the viruses applied to the control slide were recovered from the control smear. This indicates that drying inactivated a portion of the viruses. However, no viruses were recovered when the smears were scrubbed off with 0.4% docusate sodium solution.

Although the embodiments of the method of this invention are described above with reference to Herpes Simplex virus, Rotavirus, Influenza A virus, Adenovirus, and Coxsackievirus, the methods and compositions of this invention can be used for treatment of other viral infections as well. For example, viral infections caused by Herpes virus other than Herpes Simplex such as Epstein-Barr, Varicella-Zoster and Cytomegalovirus can be treated in accordance with this method. Also, viral infections caused by other enveloped viruses such as Orthomyxovirus (Influenza B and C), Poxvirus, Paramyxovirus, Coronavirus, Rhabdovirus, Togavirus, Bunyavirus, Arenavirus, Rubella, Hepatitis B virus and Retroviruses including HTLV III virus as well as non-enveloped viruses in addition to Adenovirus and the like can be treated in accordance with practice of principles of the method of this invention.

The above descriptions of exemplary embodiments of the methods and compositions for treating viral infections are for illustrative purposes. Because of variations, which will be apparent to those skilled in the art, the present invention is not intended to be limited to the particular embodiments described above. The scope of the invention is defined in the following claims.

What is claimed is:

1. A method for treating viral infections of animals and humans caused by an enveloped virus, the method comprising the steps of administering to a human or animal infected with said enveloped virus an anti-viral dosage of a compound of the following formula:

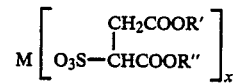

wherein R' and R'' are each independently a straight chain or branched chain alkyl group having from 5 to 8 carbon atoms, M is Na, K or Ca, and x is 1 when M is Na or K and x is 2 when M is Ca.

2. The method according to claim 1 wherein the anti-viral compound is dioctyl sodium sulfosuccinate.

3. The method according to claim 2 wherein the effective anti-viral dosage of dioctyl sodium sulfosuccinate is administered orally.

4. The method according to claim 2 wherein the effective anti-viral dosage of dioctyl sodium sulfosuccinate is administered topically.

5. The method according to claim 2 wherein the effective anti-viral dosage of dioctyl sodium sulfosuccinate is from 5 mgs to about 35 gms per day in a delivery system which assures a systemic or local concentration of from about 0.01 to about 0.2 mg of said dioctyl sodium sulfosuccinate per ml of body fluids of said humans and animals at the cellular level.

6. The method according to claim 1 wherein the enveloped virus is selected from the group consisting of HSV-1, HSV-2, Influenza A virus, Respiratory Syncytial virus, and Cytomegalovirus.

7. The method according to claim 1 wherein the enveloped virus is selected from the group consisting of a Herpes virus, Paramyxovirus, Poxvirus, Orthomyxovirus, Coronavirus, Rhabdovirus, Togavirus, Bunyavirus, Arenavirus, Rubella virus, Hepatitis B virus, and HTLV III virus.

8. A method for inactivating Herpes Simples virus within a human host comprising the steps of contacting the Herpes Simplex virus with dioctyl sodium sulfosuccinate by providing the dioctyl sodium sulfosuccinate in fluids of the human host at a concentration of from about 0.01 to about 0.2 mg of said dioctyl sodium sulfosuccinate per ml of said fluids at the cellular level.

9. A method for preventing an enveloped virus from infecting a cell in a human or animal host, the method comprising the steps of administering to a human or animal host susceptible to infection by such an enveloped virus a systemic or local dosage of a compound of the following formula:

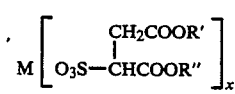

wherein R' and R'' are each independently a straight chain or branched chain alkyl group having from 5 to 8 carbon atoms, M is Na, K or Ca, and x is 1 when M is Na or K and x is 2 when M is Ca, said compound thereby contacting such a cell in the human or animal host in fluid solution wherein the compound is provided in such a fluid solution at a systemic or local concentration of from about 0.01 to about 0.2 mg of said compound per ml of said fluid solution at the cellular level.

10. The method according to claim 9 wherein the anti-viral compound is dioctyl sodium sulfosuccinate.

11. The method according to claim 9 wherein such an animal host is a bovine host.

12. A method for preventing an enveloped virus from infecting a human or animal host susceptible to said enveloped virus, the method comprising the steps of administering a systemic or local dosage of a compound of the formula:

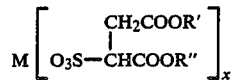

wherein R' and R" are each independently a straight chain or branched chain alkyl group having from 5 to 8 carbon atoms, M is Na, K or Ca, and x is 1 when M is Na or K and x is 2 when M is Ca, said compound administered in an amount effective for preventing infection by the enveloped virus to a person or animal susceptible to the infection by said enveloped virus.

13. The method according to claim 12 wherein the anti-viral compound is dioctyl sodium sulfosuccinate.

14. The method according to claim 13 wherein the effective dosage is from 5 mgs to about 35 gms per day in a delivery system which assures a systemic or local concentration of between about 0.01 and 0.2 mg of said dioctyl sodium sulfosuccinate per ml of fluids on a cellular level.

15. The method according to claim 12 wherein the effective dosage is administered orally.

16. The method according to claim 12 wherein the enveloped virus is selected from the group consisting of Herpes virus, Paramyxovirus, Poxvirus, Orthomyxovirus, Coronavirus, Rhabdovirus, Togavirus, Bunyavirus, Arenavirus, Rubella virus, Hepatitis B virus, and HTLV III virus.

17. A method for preventing Rotavirus from infecting a cell in a human or animal host susceptible to infection by Rotavirus, the method comprising the steps of administering a systemic or local dosage of dioctyl sodium sulfosuccinate to the human or animal host for contacting such a cell in the human or animal host with said dioctyl sodium sulfosuccinate in fluid solution, the dioctyl sodium sulfosuccinate being provided in such a fluid solution at a systemic or local concentration of from about 0.01 to about 0.2 mg per ml of said fluid solution at the cellular level.

18. A method for inactivating a virus selected from the group consisting of Herpes virus, Paramyxovirus, Poxvirus, Orthomyxovirus, Coronavirus, Rhabdovirus, Togavirus, Bunyavirus, Arenavirus, Rubella virus, Hepatitis B virus, and HTLV III virus in a human host, the method comprising the steps of contacting such a virus with dioctyl sodium sulfosuccinate by providing the dioctyl sodium sulfosuccinate in fluids of the human host at a concentration of from about 0.01 to about 0.2 mg of said dioctyl sodium sulfosuccinate per ml of said fluids at the cellular level.

19. A method for treating a human or animal host having a viral infection caused by an enveloped virus, the method comprising the steps of topically applying to an area of human or animal tissue containing such an enveloped virus a composition containing an effective anti-viral amount of a compound of the following formula:

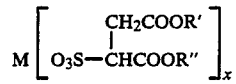

wherein R' and R" are each independently a straight chain or branched chain alkyl group having from 5 to 8 carbon atoms, M is Na, K or Ca, and x is 1 when M is Na or K and x is 2 when M is Ca, said compound thereby contacting the virus in a virucidally effective amount.

20. The method according to claim 19 wherein the anti-viral compound is dioctyl sodium sulfosuccinate.

21. The method according to claim 20 wherein the composition comprises from about 0.01% by weight to about 1% by weight of dioctyl sodium sulfosuccinate based on the total weight of the composition.

22. The method according to claim 19 wherein the enveloped virus is selected from the group consisting of Herpes virus, Paramyxovirus, Poxvirus, Orthomyxovirus, Coronavirus, Rhabdovirus, Togavirus, Bunyavirus, Arenavirus, Rubella virus, Hepatitis B virus, and HTLV III virus.

23. The method according to claim 19 wherein the composition is selected from the group consisting of a lotion, a cream, a dusting powder, a bronchial inhalation spray, a mouthwash, a cleanser, and a douche.

24. A method for inactivating an enveloped virus contained in a volume of human or animal blood, plasma, serum or products derived therefrom, the method comprising the steps of contacting an enveloped virus contained in said blood, plasma, serum or products derived therefrom with an amount of dioctyl sodium sulfosuccinate sufficient to inactivate such an enveloped virus.

25. The method according to claim 24 wherein the enveloped virus is selected from the group consisting of HTLV III virus and Hepatitis B virus.

26. A method for inactivating an enveloped virus on a inanimate surface, the method comprising the steps of contacting such an enveloped virus on a surface with an anti-virally effective amount of a compound of the following formula:

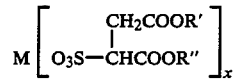

wherein R' and R" are each independently a straight chain or branched chain alkyl group having from 5 to 8 carbon atoms, M is NH4, Na, K or Ca, and x is 1 when M is NH4, Na or K, and x is 2 when M is Ca.

27. The method according to claim 26 wherein the anti-viral compound is dioctyl sodium sulfosuccinate.

28. A virucidal product comprising a web substrate containing a virucidally effective amount of dioctyl sodium sulfosuccinate.

29. The product according to claim 28 wherein the substrate is selected from cellulose tissue, non-woven fabrics and textile materials.

30. The product according to claim 28 wherein dioxtyl sodium sulfosuccinate is present in an amount of from about 0.01% to about 3% or more by weight relative to the total weight of dioctyl sodium sulfosuccinate and the substrate.

31. A virucidal cleanser for use on animals or humans, the cleanser comprising a virucidally effective amount of dioctyl sodium sulfosuccinate in a physiologically acceptable carrier.

32. The virucidal cleanser according to claim 31 wherein dioctyl sodium sulfosuccinate is provided at a concentration of from about 0.001% to at least about 1% by weight relative to the total weight of the cleanser.

33. A sanitizer for use in disinfecting surfaces comprising a virucidally effective amount of a compound of the following formula:

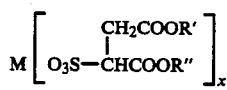

wherein R' and R'' are each independently a straight chain or branched chain alkyl group having from 5 to 8 carbon atoms, M is $NH_4$, Na, K or Ca, and x is 1 when M is $NH_4$, Na or K, and x is 2 when M is Ca.

34. A method for treating viral infections of animals and humans caused by an enveloped virus, the method comprising the steps of administering to a human or animal infected with said enveloped virus an anti-viral dosage of a composition consisting essentially of a compound of the following formula:

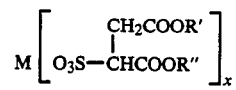

wherein R' and R'' are each independently a straight chain or branched chain alkyl group having from 5 to 8 carbon atoms, M is Na, K or Ca, and x is 1 when M is Na or K and x is 2 when M is Ca.

35. The method according to claim 34 wherein the anti-viral compound is dioctyl sodium sulfosuccinate.

36. The method according to claim 35 wherein the effective anti-viral dosage of dioctyl sodium sulfosuccinate is administered orally.

37. The method according to claim 35 wherein the effective anti-viral dosage of dioctyl sodium sulfosuccinate is administered topically.

* * * * *